United States Patent [19]
Cipollina et al.

[11] Patent Number: 5,607,961
[45] Date of Patent: Mar. 4, 1997

[54] ANTIDEPRESSANT 3-(AMINOCYCLOALKENYL)-INDOLE-5-NITRILE DERIVATIVES

[75] Inventors: Joseph A. Cipollina, Middletown; Ronald J. Mattson, Meriden; Charles P. Sloan, Wallingford, all of Conn.

[73] Assignee: Bristol-Myers Squibb Company, New York, N.Y.

[21] Appl. No.: 517,999

[22] Filed: Aug. 22, 1995

Related U.S. Application Data

[62] Division of Ser. No. 178,073, Jan. 6, 1994, Pat. No. 5,468,767.

[51] Int. Cl.$^6$ .................................... A61K 31/405
[52] U.S. Cl. .................... 514/415; 548/503; 548/504; 548/454
[58] Field of Search .................... 514/414, 415; 548/503, 504, 505, 469

[56] References Cited

U.S. PATENT DOCUMENTS

| | | | |
|---|---|---|---|
| 4,954,502 | 9/1990 | Smith et al. | 514/253 |
| 5,124,332 | 6/1992 | Wise et al. | 514/253 |
| 5,245,046 | 9/1993 | Youngdale et al. | 548/495 |
| 5,468,768 | 11/1995 | Cipollina et al. | 514/415 |

FOREIGN PATENT DOCUMENTS

| | | |
|---|---|---|
| 0560669 | 9/1993 | European Pat. Off. . |
| 2458550 | 1/1981 | France . |
| 9310092 | 5/1993 | WIPO . |

*Primary Examiner*—Charles T. Jordan
*Assistant Examiner*—John R. Hardee
*Attorney, Agent, or Firm*—Richard P. Ryan

[57] ABSTRACT

Certain 3-amino-cycloalkanyl and cycloalkenyl derivatives of 5-cyano-substituted indoles of Formula I are useful antidepressant agents.

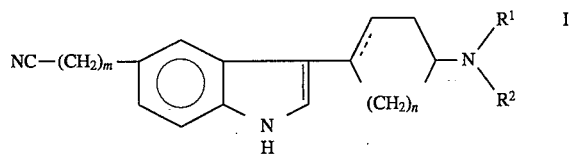

The substituent $R^1$ is hydrogen or $C_{1-4}$ alkyl and $R^2$ is $C_{1-4}$ alkyl or —$(CH_2)_p$—Ar with Ar being a phenyl, pyridinyl, pyrimidinyl or 1,4-benzodioxan-2-yl moiety. The symbol m is zero or 1, n is 1 to 3 and p is zero or 1 to 4.

7 Claims, No Drawings

ANTIDEPRESSANT 3-(AMINOCYCLOALKENYL)-INDOLE-5-NITRILE DERIVATIVES

CROSS-REFERENCE TO RELATED APPLICATION(S)

This is a division of application(s) U.S. Ser. No. 08/178,073 filed Jan. 6, 1994, now U.S. Pat. No. 5,468,767.

BACKGROUND OF THE INVENTION

This invention generally pertains to heterocyclic carbon compounds having drug and bio-affecting properties and to their preparation and use. In particular, the invention is concerned with disubstituted cycloalkanyl and cycloalkenyl derivatives wherein one substituent moiety is an indol-3-yl-5-nitrile group and the other moiety is an alkyl, awl or heteroaryl, e.g. pyridinyl, amino group. These compounds are potent serotonin uptake inhibitors which renders them useful as antidepressant agents.

Several series of compounds comprising a central cycloalkanyl or cycloalkenyl ring linked both to an indole group and to an amine containing functionality have been reported.

Smith, et al. in U.S. Pat. No. 4,954,502 disclosed compounds of formula (i) having antidepressant properties. In these compounds $R^3$ and $R^4$ are

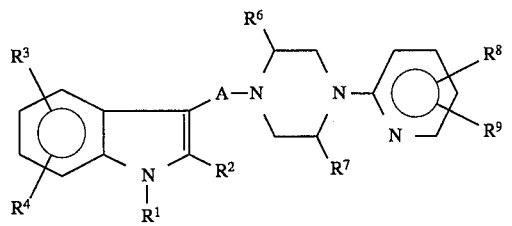

not nitrile functionalities but A was, inter alia, a 5 to 7 carbon cycloalkanyl or cycloalkenyl ring.

Wise, et al. in U.S. Pat. No. 5,124,332 described compounds of formula (ii) as being useful for central nervous system disorders, including depression.

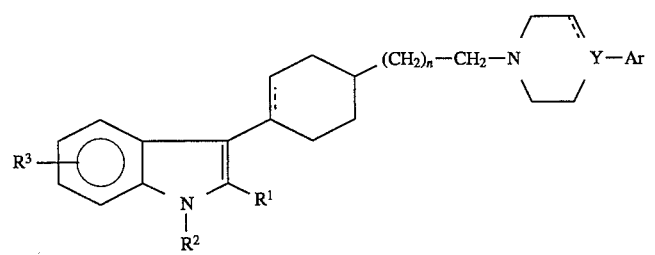

In formula (ii), $R^3$ was not a nitrile moiety and Y could be C or N.

Mattson, et al. in EP 0560669A disclosed antipsychotic agents of formula (iii).

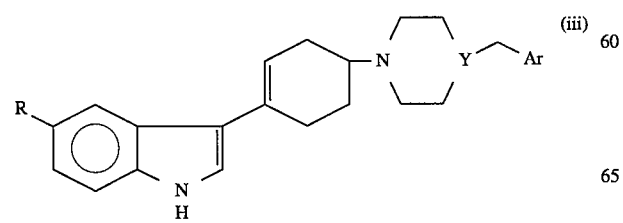

In formula (iii), R was not a nitrile functionality and Y could be C or N.

Caprathe, et al. in WO 93/10092 disclosed a series of compounds, including those of formula (iv), as dopaminergic

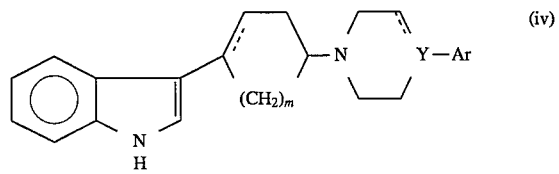

agents useful in treating psychosis and CNS disorders involving disturbances in dopamine transmission.

Of less relevance are the neuroleptic and antiemetic compounds of formula (v) disclosed in Fr 2,458,550 for Roussel-Uclaf.

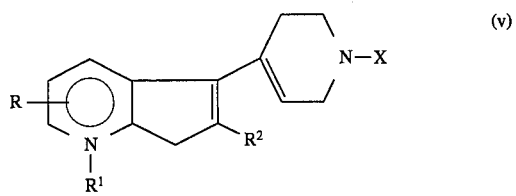

In formula (v), X is, inter alia, a phenalkyl group.

The foregoing references do not teach nor suggest the specific combination of structural variations that comprise the compounds of the present invention and their use as antidepressant agents.

SUMMARY AND DETAILED DESCRIPTION OF THE INVENTION

The present invention relates to novel 3-amino-cycloalkanyl and cycloalkenyl derivatives of 5-cyano-substituted indoles; their therapeutic use as serotonin re-uptake inhibitors, particularly for treatment of depression; and their pharmaceutical compositions.

In a broad aspect, the present invention concerns 5-cyano-substituted indol-3-ylcycloalkanyl- and cycloalkenyl-amine derivatives causing potent inhibition of serotonin re-uptake and characterized by Formula I.

$$\text{NC—(CH}_2)_m\text{—[indole]—[cycloalkenyl (CH}_2)_n\text{]—N}R^1R^2 \quad \text{I}$$

In Formula I, $R^1$ is hydrogen or $C_{1-4}$ alkyl and $R^2$ is $C_{1-4}$ alkyl or —(CH$_2$)p—Ar.

The symbol m is zero or 1; n is an integer from 1 to 3; and p is zero or an integer from 1 to 4.

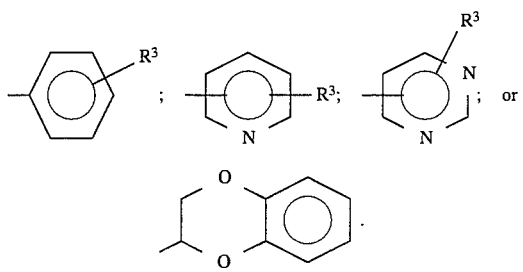

$R^3$ is hydrogen, halogen or $C_{1-4}$ alkoxy.

Finally, the solid plus dotted line is meant to represent either a single or a double covalent bond.

Additionally, compounds of Formula I also encompass all pharmaceutically acceptable acid addition salts and/or solvates thereof. The present invention is also considered to include stereoisomers including geometric as well as optical isomers, e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art.

The term "$C_{1-4}$" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl. "Halogen" is fluorine, chlorine, bromine, or iodine.

Preferred compounds are those wherein m is zero, n is 2, and $R^2$

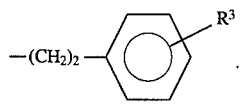

The pharmaceutically acceptable acid addition salts of the invention are those in which the counter ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

The compounds of formula I can be prepared by adaptation of the general synthetic processes shown in Schemes 1 and 2. In Scheme 1, an appropriately substituted indole (III) is condensed with a cycloalkanone intermediate of formula II to give the cycloalkenyl product IB. Reduction of IB provides the cycloalkanyl product IA.

Scheme 2 sets forth the general method for synthesis of the cycloalkanone intermediates (II). Reductive amination of an appropriate cycloalkanedione-mono-ethylene ketal (VI) and an amine (V) using a reagent such as sodium triacetoxyborohydride affords ketal-amine intermediates of formula IVa (wherein $R^1$=H) or IVb (wherein $R^1$=lower alkyl). A second reductive amination, if desired, of IVa and an appropriate aldehyde gives the ketal-amine intermediate IVb with $R^4$ being hydrogen or $C_{1-3}$ alkyl. The choice of (IVa) or (IVb) depends on whether a primary amine (Va) or a secondary amine (Vb) is used in the reductive amination. Removal of the ketal group under acidic conditions gives the cycloalkanone-amine intermediate (II) in high yields.

SCHEME 1

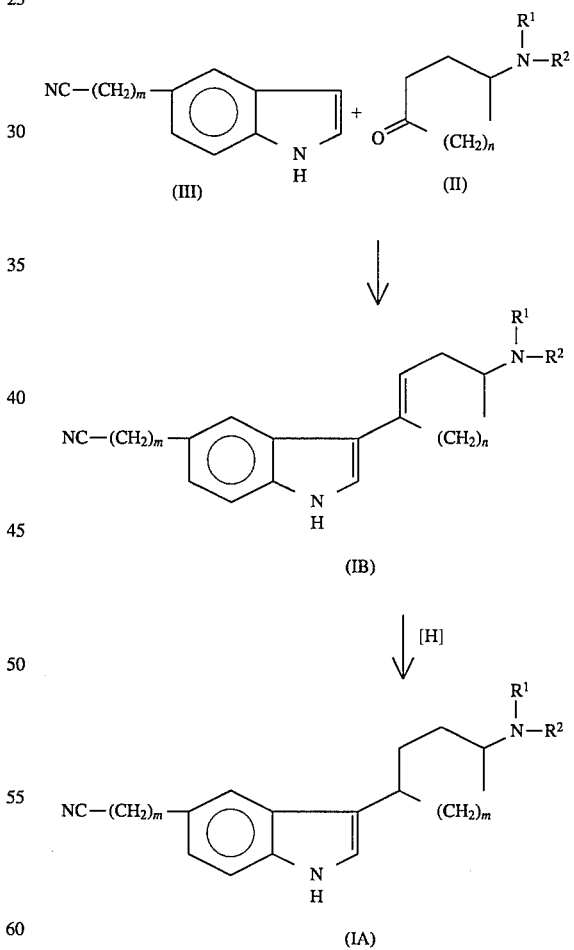

Scheme 2

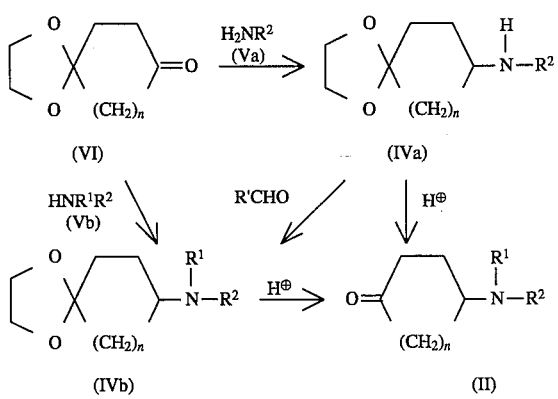

The reactions employed in Schemes 1 and 2 and their application are familiar to the practitioner skilled in organic synthesis and modifications of conditions and reagents would be readily understood. The skilled synthetic chemist would know how to adapt these processes for preparation of specific Formula I compound including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

The compounds of Formula I show potent inhibition of 5-HT re-uptake and can be envisioned as potential agents for disorders associated with dysfunction in serotonergic neurotransmission. Such disorders may include depression, anxiety, eating disorders, obesity, and drug abuse. In particular, the active compounds of the instant series are envisioned as specific agents for treating depression.

The compounds comprising the present invention inhibit the re-uptake of endogenous serotonin. Selective inhibitors of serotonin uptake are effective for the treatment of mental depression and have been reported to be useful for treating chronic pain (see: R. W. Fuller, Pharmacologic Modification of Serotonergic Function: Drugs for the Study and Treatment of Psychiatric and Other Disorders," *J. Clin. Psychiatry,* 47:4 (Suppl.) April 1986, pp. 4–8). Compounds of the present invention are also envisioned to be useful in the following disorders: obsessive-compulsive disorder, feeding disorders, anxiety disorders and panic disorders.

Determination of endogenous monoaminergic re-uptake inhibition values both for serotonin and norepinephrine was accomplished using test methods described by P. Skolnick, et al., *Br. J. Pharmacology,* (1985), 86, pp. 637–644; with only minor modifications. In vitro $IC_{50}$ (nM) test values were determined for representative compounds of Formula I based on their inhibition of synaptosomal re-uptake of tritiated serotonin. Test data $IC_{50}$ values lower than 500 nM are considered to reflect activity as an inhibitor of serotonin re-uptake. Compounds with $IC_{50}$ values lower than 100 nM comprise preferred compounds and those with $IC_{50}$ value less than 10 nM are most preferred.

Another aspect of the instant invention provides a method for treating a mammal afflicted with depression or chronic pain which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound fluoxetine, cf: Schatzberg, et al., *J. Clin. Psychopharmacology* 7/6 Suppl. (1987) pp. 4451–4495, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts (δ) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$).

Analytical thin-layer chromatography (TLC) was performed on 0.25 mm EM silica gel 60 F-254 coated glass plates and preparative flash chromatography was performed on EM silica gel (36–62 μm). The solvent systems used are reported where appropriate. All reaction, extraction and chromatography solvents were reagent grade and used without further purification except tetrahydrofuran (THF) which was distilled from sodium/benzophenone ketyl. All non-aqueous reactions were carried out in flame-dried glassware under a nitrogen atmosphere.

A. Synthesis of Intermediates

Compounds of Formula II

General Procedure

Equivalent molar amounts of a cycloalkanedione monoethylene ketal (VI) and an amine (V) are combined in methylene chloride under $N_2$ at room temperature. A reaction solvent volume of approximately 400 mL $CH_2Cl_2$ per 25 g amounts of VI is the amount generally employed. Sodium triacetoxyborohydrige (1.25 to 1.50 equivalent per one equivalent of amine) is added in portions, taking care to avoid boilover. The reaction is stirred until TLC examination indicates consumption of starting materials. The reaction is then cooled in an ice-water bath and made basic by the addition of 3N NaOH. The layers are separated and the aqueous phase is extracted with $CH_2Cl_2$ (2×). The organic fractions are collectively dried over $Na_2SO_4$, filtered, and the solvent is removed in vacuo. The crude product (IV), which is usually quite pure, is then hydrolyzed.

The crude ketal (IV) is dissolved in 50% $H_2SO_4$ (10 mL/g ketal) at room temperature. An equivalent volume of THF is added and the reaction is allowed to stir at room temperature for 18 h. The reaction is cooled is an ice-water bath and, with vigorous stirring, is made strongly basic by the dropwise addition of 50% NaOH. The supernatant is decanted into a separatory funnel and the layers are separated. The aqueous layer is repeatedly extracted with diethyl ether (~5×) with warm water being added to prevent further salt precipitation. The combined organic fractions are back-extracted with brine, dried over $MgSO_4$, filtered and the solvents are removed in vacuo. The crude products are purified by bulb-to-bulb distillation under vacuum (see Table 1).

TABLE 1

Synthesis of Aminocycloalkanones of Formula II

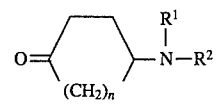

| Ex # | R¹ | R² | bp (°C. at 5–9 mm)ᵃ | % Yield (2 steps) |
|---|---|---|---|---|
| 1 | Me | Me | 60–5 | 41 |
| 2 | Et | Et | 70–5 | 35 |
| 3 | Pr | Pr | 115–120 (at 0.1 mm) | 22 |
| 4 | i-Pr | H | NP | 74 |
| 5 | H | Ph | (mp 116–7) | 98 |
| 6 | H | p-F-Ph | (mp 123–4) | 99 |
| 7 | H | $CH_2Ph$ | 160–70 | 69 |
| 8 | H | $-(CH_2)_2Ph$ | 120–30 | 89 |
| 9 | Me | $-(CH_2)_2Ph$ | 130–40 | 53 |
| 10 | H | o-F-Ph-$(CH_2)_2-$ | 190–200 | 51 |
| 11 | H | m-F-Ph$(CH_2)_2-$ | NP | 89 |
| 12 | H | p-F-Ph$(CH_2)_2-$ | 180–90 | 52 |
| 13 | H | o-OMe-Ph$(CH_2)_2-$ | NP | 99 |
| 14 | H | m-OMe-Ph$(CH_2)_2-$ | NP | 96 |
| 15 | H | p-OMe-Ph$(CH_2)_2-$ | 190–200 | 52 |
| 16 | H | 3-pyridinyl$(CH_2)_2-$ | 190–200 | 50 |
| 17 | H | 2-pyridinyl$(CH_2)_2-$ | NP | 55 |
| 18 | H | Ph$(CH_2)_3-$ | 180–90 | 63 |
| 19 | H | Ph$(CH_2)_4-$ | 170–80 | 71 |
| 20 | H | 1,4-benzodioxan-2-yl | NP | 89 |
| 21 | H | Et | 80–90 | 80 |

ᵃCompounds were purified by kugelrohr bulb-to-bulb distillation under reduced pressure. Reported temperatures indicate pot temperature at which product was collected. NP = not purified; in these instances, compounds were either clean enough to use in their crude reaction form or they were flash chromatographed.

Compounds of Formula III

Most indoles with 5-substituents containing a cyano group are known and can be readily prepared from literature procedures with some of these indoles also being commercially available.

Synthesis of Products of Formula I

General Procedure for the Condensation of Indoles (III) with Cycloalkanones (II)

An appropriate indole (III; 1.0 equiv.) and cycloalkanone (II; 1.05 equiv.) are stirred in alcohol, preferably ethanol (0 to 20 mL/g of indole, III) under $N_2$. Pyrrolidine (2.5 equiv.) is added and the reaction is refluxed for 18–48 hr utilizing TLC examination to indicate reaction completion. The Formula IB products are recognizable on TLC due to their tendency to fluoresce in UV light as opposed to the reaction starting materials. Decomposition is indicated by the appearance of other dark blue spots (nonfluorescent).

The reaction is worked up by removal of solvent and excess pyrrolidine in vacuo. The residual oils are then purified by gradient flash chromatography using a 2–10% methanol in $CH_2Cl_2$ gradient system with an added 0.2% of $NH_4OH$. The purified base forms can be converted to acid salt forms utilizing standard salt forming procedures.

This procedure is more fully demonstrated by the following exemplification.

EXAMPLE 22

3-[[4-(2-Phenylethyl)amino]-1-cyclohexen-1-yl]-1H-indole-5-acetonitrile 1H-indole-5-acetonitrile¹ (0.25 g, 0.0016 mol), 4-[(2-phenylethyl)amino]cyclohexanone (0.522 g, 0.0024 mol) and pyrrolidine (0.5 mL) were dissolved in EtOH (80 mL) and refluxed for 24 h. A TLC (silica gel, 50% EtOAc in Hexane) showed that the reaction was not occurring, thus, the solvent volume was reduced in vacuo to a final volume of 5 mL. An additional equivalent of 4-[(2-phenylethyl)amino]cyclohexanone (0.0024 mol) and pyrrolidine (2 mL) was added. The reaction was heated at reflux for 4 h. The solvent was removed in vacuo. Silica gel chromatography (95:5:0.5 $CH_2Cl_2$—MeOH—$NH_4OH$) of the residue yielded the product (0.275 g, 35%). The viscous yellow oil was dissolved in EtOAc and treated with fumaric acid in MeOH to afford the fumarate salt (0.132 g, 40%): mp 238°–242° C. Anal. Calcd for $C_{24}H_{25}N_3 \cdot 0.6C_4H_4O_4$: C 74.59; H 6.50; N 9.88. Found: C 74.66; H 6.61; N 9.80.

[1]Indole-5-acetonitrile was prepared according to Naruto and Yonemitsu, Chem. Pharm. Bull., 1972, 20 (10), 2163.

By appropriate modification of this condensation reaction, additional Formula IB products are readily prepared. Some additional Formula IB products are shown in Table 2.

TABLE 2

Additional Products of Formula 1B

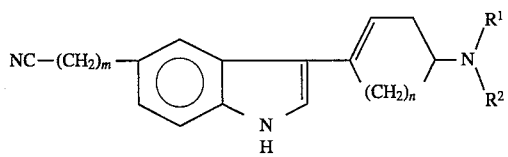

| Ex # | $R^1$ | $R^2$ | m | n | mp (°C.) | Analytical Formula |
|---|---|---|---|---|---|---|
| 23 | Me | Me | 0 | 2 | >225 | $C_{17}H_{19}N_3/1.2$ HCl/ 0.1 $H_2O$/0.2 $C_3H_8O$ |
| 24 | Et | Et | 0 | 2 | >225 | $C_{19}H_{23}N_3$/HCl/0.1 $H_2O$ |
| 25 | Pr | Pr | 0 | 2 | >230 | $C_{21}H_{27}N_3$/0.5 $C_4H_4O_4$ |
| 26 | i-Pr | H | 0 | 2 | 158 | $C_{18}H_{21}N_3$ |
| 27 | H | $PhCH_2$ | 0 | 2 | 220.5 | $C_{22}H_{21}N_3$/ 1.1 $C_2H_2O_4$/0.2 $H_2O$ |
| 28 | H | $Ph(CH_2)_2$ | 0 | 2 | >225 | $C_{23}H_{23}N_3$/HCl/0.1 $H_2O$ |
| 29 | Me | $Ph(CH_2)_n$ | 0 | 2 | 148(d) | $C_{24}H_{25}N_3$/0.6 $C_4H_4O_4$ |
| 30 | H | m-F-$Ph(CH_2)_2$ | 0 | 2 | >250 | $C_{23}H_{22}N_3F$/HCl |
| 31 | H | $Ph(CH_2)_2$ | 1 | 2 | 238–42 | $C_{24}H_{25}N_3$/0.6 $C_4H_4O_4$ |
| 32 | H | o-F-$Ph(CH_2)_2$ | 0 | 2 | >220 | $C_{23}H_{22}N_3F$/0.6 $C_4H_4O_4$ |
| 33 | H | p-F-$Ph(CH_2)_2$ | 0 | 2 | >240 | $C_{23}H_{22}N_3F$/1.3 HCl |
| 34 | H | o-OMe-$Ph(CH_2)_2$ | 0 | 2 | 235–40(d) | $C_{24}H_{25}N_3O$/HCl |
| 35 | H | m-OMe-$Ph(CH_2)_2$ | 0 | 2 | >250 | $C_{24}H_{25}N_3O$/HCl |
| 36 | H | p-OMe-$Ph(CH_2)_2$ | 0 | 2 | >220 | $C_{24}H_{25}N_3O$/HCl/0.2 $H_2O$ |
| 37 | H | 3-pyridinyl$(CH_2)_2$ | 0 | 2 | >225 | $C_{22}H_{22}N_4$/0.5 $C_4H_4O_4$ |
| 38 | H | $Ph(CH_2)_3$ | 0 | 2 | 162-4 | $C_{24}H_{25}N_3$ |
| 39 | H | benzodioxolylmethyl | 0 | 2 | 246(d) | $C_{24}H_{23}N_3O_2$/ 0.8 $C_2H_2O_4$ |
| 40 | H | $Ph(CH_2)_4$ | 0 | 2 | >225 | $C_{25}H_{27}N_3$/0.5 $C_4H_4O_4$ |
| 41 | H | Et | 0 | 2 | 172–3 | $C_{17}H_{19}N_3$/0.04 $C_2H_6O$ |

General Procedure for the Reduction of IB Compounds to IA Compounds

Any of the cycloalkenyl products (IB) as synthesized above can readily be converted into cycloalkanyl products (IA) by standard hydrogenation procedures to give a mixture of cis- and trans- ring products.

As an example, 3-[4-[N-(2-phenylethyl)amino]cyclohexanyl]-1H-indole-5-nitrile can be reduced in ethanol under low pressure hydrogenation utilizing palladium or carbon as a catalyst. Purification by means of flash chromatography provides cis- and trans- product.

Some representative IB compounds and their inhibition of 5-HT uptake activity are given in Table 3. In vitro $IC_{50}$ (nM) test values below 100 nM are designated with  and those below 10 nM with *.

TABLE 3

Inhibition of Serotonin Re-Uptake by Formula I Compounds

| Example | Uptake Inhibition |
|---|---|
| 23 | *** |
| 24 | ** |
| 26 | ** |
| 27 | *** |
| 28 | *** |
| 29 | *** |
| 30 | *** |
| 31 | ** |
| 32 | *** |
| 33 | *** |
| 34 | *** |
| 35 | *** |
| 36 | *** |
| 37 | *** |
| 38 | *** |
| 39 | *** |
| 40 | *** |
| 41 | ** |

We claim:
1. A compound of Formula I or a pharmaceutically acceptable acid addition salt thereof

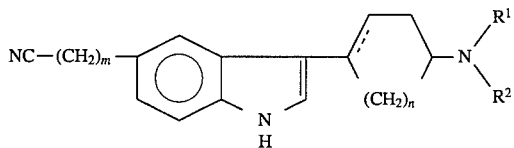

wherein
R¹ is hydrogen or $C_{1-4}$ alkyl;
R² is —$(CH_2)_p$—Ar;
m is zero or 1;
n is an integer from 1 to 3;
p is zero or an integer from 1 to 4;
Ar is

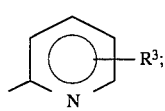

$R^3$ is hydrogen, halogen or $C_{1-4}$ alkoxy; and
the solid plus dotted line represents a single or double covalent bond.

2. A compound of claim 1 wherein m is zero.
3. A compound of claim 1 wherein n is 2.
4. A compound of claim 1 wherein p is 2.
5. The compound of claim 3 3-[4-[N-[2-(pyridin-3-yl)ethyl]amino]cyclohexen-1-yl]-1H-indole-5-nitrile.
6. A method for ameliorating a state of depression in a mammal comprising administration to the mammal of an effective antidepressant amount of a compound claimed in claim 1.
7. A pharmaceutical composition in unit dosage form suitable for systemic administration to a mammalian host comprising a pharmaceutical carrier and from about 1 to 500 mg of an antidepressant compound selected from the compounds claimed in claim 1.

* * * * *

UNITED STATES PATENT AND TRADEMARK OFFICE
CERTIFICATE OF CORRECTION

PATENT NO. : 5,607,961
DATED : 3/4/97
INVENTOR(S) : Joseph A. Cipollina et al

It is certified that error appears in the above-identified patent and that said Letters Patent are hereby corrected as shown below:

In Scheme 2 on page 5, please amend "$R^1CHO$" (over reaction arrow from (IVa) to (IVb) to --$R^ACHO$--.

Signed and Sealed this

First Day of July, 1997

Attest:

BRUCE LEHMAN

Attesting Officer    Commissioner of Patents and Trademarks